(12) United States Patent
Mount

(10) Patent No.: US 11,571,488 B2
(45) Date of Patent: Feb. 7, 2023

(54) PATHOGEN MITIGATION

(71) Applicant: Randy A. Mount, Dayton, OH (US)

(72) Inventor: Randy A. Mount, Dayton, OH (US)

( * ) Notice: Subject to any disclaimer, the term of this patent is extended or adjusted under 35 U.S.C. 154(b) by 125 days.

(21) Appl. No.: 17/221,041

(22) Filed: Apr. 2, 2021

(65) Prior Publication Data

US 2021/0220505 A1   Jul. 22, 2021

Related U.S. Application Data

(62) Division of application No. 15/938,394, filed on Mar. 28, 2018, now Pat. No. 10,967,093.

(60) Provisional application No. 62/477,724, filed on Mar. 28, 2017.

(51) Int. Cl.

| | | |
|---|---|---|
| *A61L 9/14* | (2006.01) | |
| *A61L 2/24* | (2006.01) | |
| *A61L 2/20* | (2006.01) | |
| *A61L 2/00* | (2006.01) | |
| *F24F 3/16* | (2021.01) | |
| *A61L 9/00* | (2006.01) | |
| *F24F 11/30* | (2018.01) | |
| *F24F 11/58* | (2018.01) | |
| *F24F 8/30* | (2021.01) | |

(52) U.S. Cl.
CPC ............... *A61L 9/14* (2013.01); *A61L 2/00* (2013.01); *A61L 2/0017* (2013.01); *A61L 2/0094* (2013.01); *A61L 2/208* (2013.01); *A61L 2/24* (2013.01); *A61L 9/00* (2013.01); *F24F 3/16* (2013.01); *F24F 8/30* (2021.01); *F24F 11/30* (2018.01); *F24F 11/58* (2018.01)

(58) Field of Classification Search
CPC ..... A61L 2/00; A61L 9/00; A61L 9/14; A61L 2/208; A61L 2/24; A61L 2/0017; F24F 3/16
See application file for complete search history.

(56) References Cited

U.S. PATENT DOCUMENTS

2016/0041074 A1 * 2/2016 Pliskin ................ G01N 1/2273
422/3

\* cited by examiner

*Primary Examiner* — Sean E Conley
(74) *Attorney, Agent, or Firm* — Thomas E. Lees, LLC

(57) ABSTRACT

The mitigation of indoor pathogens comprises quantifying, using a bio-aerosol monitoring system, the amount of total pathogens in the air and on surfaces within an indoor environment. Moreover, the process comprises sanitizing the indoor environment with portable equipment to stabilize the indoor environment when it is determined that the indoor environment is contaminated. Also, the process comprises installing a purification device within a contaminated area of the indoor environment, and monitoring continuously, the indoor environment after sanitizing, for pathogens. Still further, the process comprises releasing a purifying agent upon detecting pathogens in the indoor environment, and providing periodic maintenance to the purification device.

19 Claims, 5 Drawing Sheets

PATHOGEN MITIGATION

CROSS REFERENCE TO RELATED APPLICATIONS

This application is a division of U.S. patent application Ser. No. 15/938,394, filed Mar. 28, 2018, entitled PATHOGEN MITIGATION, now allowed, which claims the benefit of U.S. Provisional Patent Application Ser. No. 62/477,724, filed Mar. 28, 2017, entitled PATHOGEN MITIGATION, the disclosures of which are hereby incorporated herein by reference.

BACKGROUND

Various aspects of the present disclosure relate generally to pathogen mitigation, and more particularly to systems and processes for the detection, reduction, and prevention of pathogens located in indoor environments.

Pathogens such as mold, mildew, or viruses can be found throughout numerous environments that are frequently encountered by people. Moreover, these pathogens have been linked to illnesses and allergy symptoms that affect some people exposed to such environments. Unfortunately, attempts to remove pathogens can, in some cases, result in the spread of the pathogens further contaminating the associated environment. Even after removal, pathogens may resurface, making the treatment of pathogens difficult and often ineffective.

BRIEF SUMMARY

According to aspects of the present disclosure, a process for mitigating indoor pathogens comprises measuring for pathogens in an indoor environment and analyzing the measurements to identify whether the indoor environment is contaminated by pathogens based upon the detection. The process also comprises performing a purification process in response to determining that the indoor environment is contaminated. Here, the purification process comprises sanitizing at least a portion of the indoor environment to mitigate contamination by the detected pathogens. The purification process also comprises selecting a purification unit for the indoor environment based upon the identified contamination. Responsive thereto, the purification unit is positioned in a suitable location in order to treat a predetermined area of the indoor environment. In this regard, the purification unit is engaged to operate after sanitizing the indoor environment and may run, for example, in a continuous manner, in an otherwise ongoing fashion, periodically, or otherwise as necessary, depending upon requirements for purification. The process still further comprises monitoring the indoor environment by measuring for pathogens in the indoor environment (e.g., in an ongoing manner), and triggering an action in response to detecting a pathogen level that exceeds a predetermined threshold.

According to further aspects of the present invention, a process for mitigating indoor pathogens comprises identifying a first occurrence of pathogens in an indoor environment by measuring for pathogens in the indoor environment. The process also comprises removing the first occurrence of pathogens by sanitizing the indoor environment where the first occurrence of pathogen is located. The process also comprises installing a purification unit in a suitable location to purify the indoor environment. The process still further comprises monitoring the indoor environment for a second occurrence of pathogens by continuously (e.g., ongoing periodic, ongoing triggered, or otherwise initiated) measuring for pathogens in the indoor environment. The process may also comprise assessing the purification unit to determine maintenance needs of the purification unit, e.g., to replace a battery, cell, filter, etc., and implementing necessary maintenance to enable continued operation thereof.

According to yet further aspects of the present disclosure, a process for mitigating (which can include remediating) indoor pathogens comprises quantifying, using a bio-aerosol monitoring system, an amount of total pathogens in the air and/or on surfaces within an indoor environment. The process also comprises sanitizing the indoor environment with portable equipment to stabilize the indoor environment in response to determining that the indoor environment is contaminated based upon the results of the quantification using the bio-aerosol monitoring system. The process also comprises installing a purification device to address a contaminated area of the indoor environment, and monitoring continuously (e.g., in a continuous manner, in an otherwise ongoing fashion, periodically, or otherwise as necessary, depending upon requirements for purification) the indoor environment after sanitizing, for pathogens. Monitoring can persist, e.g., for weeks, months, years, indefinitely, etc. Yet further, the process comprises releasing a purifying agent, e.g., periodically or otherwise upon detecting pathogens in the indoor environment. The process also comprises providing periodic maintenance to the purification device to enable continued operation thereof.

DETAILED DESCRIPTION

Figure 1:
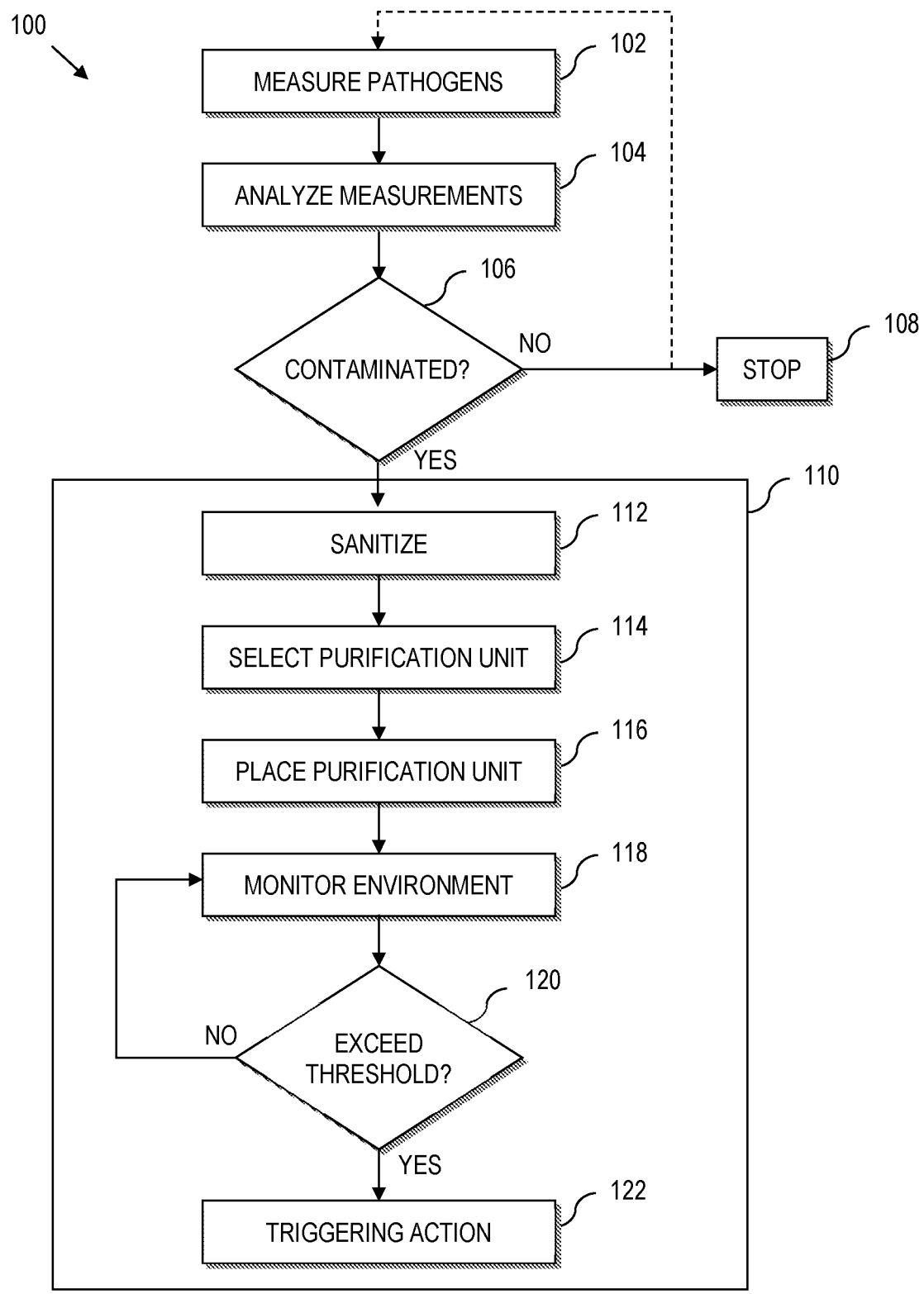
FIG. 1 is a flow chart that illustrates a process for pathogen mitigation according to an aspect of the disclosure.

The present disclosure relates to systems and processes for removing pathogens, mitigating pathogen recurrences, or both, where pathogens are found to contaminate an indoor environment.

Indoor surfaces that are touched or otherwise encountered by people create opportunities for harmful contaminants that can lead to health issues. Moreover, human contact with animals, plants, food items, microorganisms, or other articles that have contacted indoor surfaces can also create opportunities for harmful contaminants to cause health issues. Still further, harmful contaminants can be found in the air breathed within indoor environments.

In this regard, indoor contaminants can have significant consequences for businesses and industries, including but not limited to the healthcare industry and the food industry. Such indoor contaminants can result in major recalls and other mitigating actions that can be exceedingly costly and time consuming for the afflicted entity.

For instance, in the healthcare space, some reports state that hospital acquired infections (HAIs) account for 1.5 million patient infections and 75,000 deaths during hospitalization each year, amounting to $45 billion in additional costs. Major challenges include hospital patient room and intensive care unit disinfection, and device sterilization.

While food handling and healthcare industries are especially relevant, every indoor environment may be susceptible to contaminants. Other example areas that can be afflicted by contamination include, without limitation, nursing home facilities, daycare centers, sporting facilities, university buildings, office buildings, call centers, pharmaceutical facilities, clean rooms, government and public facilities, etc.

Aspects of the present disclosure provide systems and methods that utilize one or more air purification technologies, one or more surface purification technologies, combinations thereof, etc., which effectively measure and reduce harmful contamination, e.g., pathogens such as microbials, found within indoor environments. More particularly, aspects of the present disclosure measure an indoor environment for pathogens and analyze the measurements to determine whether the indoor environment is contaminated by one or more pathogens. If contamination by a pathogen is determined for the indoor environment based at least in part upon the measurements, then aspects of the present disclosure provide for sanitizing the environment to address the contamination then performing a purification process. In this regard, aspects of the present disclosure provide for ongoing treatment by continuing the purification process (e.g., over a period of time such as days, weeks, months, years, indefinitely, etc., as the application dictates) to improve the indoor environment, reduce the likelihood of pathogen reoccurrence, or both. Contamination detection, as well as a resulting purification processes are described more fully herein.

Other features, advantages, and objects of the disclosure will become apparent with reference to the following description and accompanying drawings.

Referring to the drawings and in particular FIG. 1, a process 100 for mitigating indoor pathogens is illustrated. The process 100 comprises measuring at 102 for pathogens in an indoor environment.

For the purposes of this disclosure, an indoor environment can include, but is not limited to areas within structures or partial structures such as dwellings, privately owned structures, commercial buildings, industrial buildings, storage facilities, public/governmental buildings, markets, or other areas where an individual or group of people go and/or congregate. An indoor environment can also include, but is not limited to areas within mobile structures such as containers, vessels, watercraft, over-the-road vehicles, rail vehicles, aircraft, etc.

Also, as used herein, the term "pathogen" is used generally to refer to bacteria, mold, viruses, volatile organic compounds (VOCs), odors, microbes, etc. However, the present disclosure also contemplates that a pathogen can include anything that can, or has the potential to produce an adverse effect such as illness, allergies, disease, or other negative health consequences to an individual exposed to the indoor environment, either directly or indirectly. For instance, a pathogen can comprise a virus, bacterium, prion, fungus, viroid, or parasite within the indoor environment that infects a human, animal, plant, fungus, another microorganism, etc., including viable and nonviable variants, which ultimately causes or has the potential to cause an adverse effect on an individual exposed to the indoor environment.

In an example implementation, measuring at 102 for pathogens in an indoor environment can be carried out by measuring air within or surrounding the indoor environment, by measuring surfaces and internal areas of features found within the indoor environment, combinations thereof, etc. As a few non-limiting but illustrative examples, an aerosol impactor or other form of air sampling device can be used to collect a sample of the ambient air from one or more locations within an indoor environment. The sample can be collected over any time interval as necessary to achieve a representative sampling. Moreover, the collected air sample(s) can be collected from areas within or around the indoor environment where the air is still, or in areas where there is air movement, e.g., in ductwork or in areas near doorways for ingress or egress.

Still further, samples can be collected from surfaces such as walls, ceilings, floors, furniture, equipment, products, animals, plants, or other features within the indoor environment. Yet further, samples can be collected from mobile items such as carts, containers, and other items that may be moved into and out of, the indoor environment. Also, samples can be collected from an interior of a feature. For instance, drywall located in a wall or ceiling may be pulled to reveal insulation, cladding, etc., from which one or more samples can be collected. As still another example, one or more samples can be collected from water or other fluids within the indoor environment.

In an illustrative embodiment, measuring at 102 for pathogens is accomplished using a bio-aerosol measuring system. Such a bio-aerosol measuring system can be used to monitor air in real time (or near real time). As such, continuous, real-time airborne microbial monitoring can be carried out. This avoids the need to collect samples over an extended period (although extended measurements can also/alternatively be carried out). However, the use of a bio-aerosol measuring system provides a component of a system that avoids a need to waste days awaiting culture analysis.

In a practical illustrative example implementation, an isokinetic probe is connected to a bio-aerosol monitoring system. The isokinetic probe can be used to traverse a section of ductwork within the indoor environment to detect entrained particles. The isokinetic probe can also and/or alternatively be utilized to sample ambient air within one or more regions of the indoor environment. Depending upon the application, sampling can be based upon a volume of air drawn, time to collect a sample, etc.

Yet further, sampling can be carried out by scraping a sample area, swabbing a sample area, collecting a sample into a petri dish, removing an area within the environment suspected of having a pathogen, etc. Some measurement devices may require that the sample is collected upon a sample substrate such as a slide, tape, petri dish, etc. Yet further, a combination of surface and air sampling can be utilized to measure for pathogens in the indoor environment.

An example implementation measures an amount of total pathogens (viable and nonviable) in the air, on surfaces, combinations thereof, etc., allowing the implementation to evaluate the needs of the indoor environment to be treated. In some embodiments, e.g., where measurement results can be obtained instantaneously or otherwise within a short time on site (e.g., minutes, to hours after collection), reports can be provided to an owner, custodian, or entity responsible for the indoor environment. In some embodiments where real-time or near real time analysis can be carried out, real-time insight can be provided through ongoing measurements both before and after the installation of purification units as described more fully herein.

In some embodiments, measuring at 102 for pathogens comprises measuring for a predetermined type of pathogen, e.g., a first pathogen. For instance, in some environments, a known type of undesirable pathogen can potentially be present. In some environments, a limited number of pathogen types may be at issue. Yet in other environments, pathogen types may be unknown and potentially varied. Accordingly, measurement can try to identify as many types of pathogens as within the capability of the measuring device.

As such, measuring at 102 can utilize knowledge of the indoor environment and intended uses of the indoor environment to measure for a single type of pathogen, one or more types of pathogens, any type of pathogen, or combinations thereof. Moreover, measuring at 102 can comprise measuring for a first type of pathogen (or first group of pathogen types) in the air and a second type of pathogen (or second group of pathogen types) on or in a surface, measuring for a first type of pathogen (or first group of pathogen types) in a first area and a second type of pathogen (or second group of pathogen types) in a second area, combinations thereof, etc.

The process 100 also comprises analyzing at 104, the measurements to identify whether the indoor environment is contaminated by a pathogen. The analysis can be carried out in a number of different ways. For instance, a determination of contamination may require the detection of one or more pathogens (which may comprise the same or different species). In an example embodiment, the presence of one or more pathogens is determined from the measurements at 102, based upon detecting particulate size, shape that is indicative of a pathogen, or a combination thereof. For instance, one strategy classifies particulates into categories based upon size. The classified categories are used to determine the likelihood of a pathogen of interest.

Also, the presence of a pathogen can be identified based upon one or more markers, measurements, etc., such as from image analysis, fluorescence, energy bands, or using other suitable detection technologies. As such, the detection of a pathogen need not be unconditionally verified. Rather, in an analysis based upon particulate size and/or shape, a high probability that a particulate is a pathogen may be sufficient to declare that a pathogen is present for purposes of determining whether the indoor environment is contaminated. Yet further, a classification of precise species of pathogen is not necessarily required. For instance, it may be sufficient to know that a measured particulate is a form of mold, without requiring a precise classification. In yet further embodiments, signature detection can be used to identify, e.g., at least to a statistical significance, a detected contaminant. Thus, analysis can identify an exact species, a genus, a statistical probability that a detected particulate is a pathogen, combinations thereof, etc.

Yet further, the indoor environment can be declared contaminated based upon any number of predefined conditions. For instance, in an example embodiment, the indoor environment is declared contaminated if a total pathogen count (regardless of type of pathogen) exceeds a predetermined level (e.g., concentration, total count, combination thereof, etc.). In another example embodiment, the indoor environment is declared contaminated if a single particulate of a specific pathogen (e.g., *Stachybotrys chartarum*) is identified.

In some embodiments, the presence of a single particulate of a pathogen may be sufficient to determine that the indoor environment is contaminated. In other embodiments, an indoor environment can be judged to be contaminated based upon other metrics, e.g., exceeding a predetermined concentration of pathogens, exceeding a predetermined quantity of pathogens over a sample or number of samples, over a predetermined period of time, or other suitable unit of measure, etc.

Continuing to reference FIG. 1, a decision is made at 106 as to whether the indoor environment is contaminated. If no contamination is detected, then the process may stop at 108. In some embodiments, e.g., where continued monitoring is carried out, the process may loop back to measure pathogens at 102 or perform some other process.

The process 100 also comprises performing at 110, a purification process in response to determining that the indoor environment is contaminated. The purification process can be utilized to stabilize, eradicate, clean to an acceptable limit, or otherwise address the detected contamination within the indoor environment.

For instance, as illustrated, the example purification process at 110 comprises sanitizing at 112 at least a portion of the indoor environment to mitigate contamination of detected pathogens. By way of illustration, sanitization includes, but is not limited to total removal of the pathogen from the environment, neutralizing the pathogen (physically, chemically, or both), or stabilizing the environment space. For instance, in an example implementation, neutralizing the pathogen includes using physical means, chemical means, or both to alter or destroy the structure of the pathogen, render the pathogen inert, render the pathogen nonviable, etc.

For the purposes of this disclosure, stabilizing the environment includes removal of the pathogen from the environment, reducing the amount of pathogens to a pre-determined threshold, or manipulating the environment to reduce or eliminate the effects of a pathogen. The specific techniques and equipment involved in the sanitization process can vary based on the type of pathogen(s) identified during the measurement at 102 and analysis at 104, as well as circumstances of the indoor environment.

For example, passive and active filters can be utilized in some embodiments, which utilize ozone gas or vaporized hydrogen to eliminate pathogens such as microbes or bacteria.

Some research has suggested these gases may be harmful to humans if their exposure to these gases rises above certain levels cited by the Environmental Protection Agency (EPA). Thus, in some embodiments, e.g., where humans will be in the indoor environment during sanitizing, stabilizing the indoor environment comprises using hydrogen peroxide gas and/or bi-polar ionization to eliminate pathogens, without causing harm or irritation to the surrounding people. This approach may have the beneficial side effect of diffusing into cracks and crevices in that environment to increase the effectiveness of the sanitization.

Thus, in some embodiments of the present disclosure, the process comprises deploying charged ions and hydrogen peroxide gas that attack pathogens (which may include rendering such pathogens non-viable, inert, etc.). Such charged ions and hydrogen peroxide gas in some embodiments, diffuses into cracks and crevices. Some embodiments may even utilize charged ions and hydrogen peroxide gas that diffuses through permeable walls.

Such an approach enables humans to be present while such systems are working. Moreover, such systems can reduce air and surface contaminants, e.g., by up to 99.9%.

The purification process at 110 also comprises selecting at 114, a purification unit for the indoor environment to mitigate contamination caused by the detected pathogens. For the purposes of this disclosure, mitigation can include one or more of prevention, elimination, collection, entrapment, neutralization, removal, as well as the disclosed items under sanitizing at 112. The type, size, and number of purification unit(s) selected are influenced by the aforementioned analysis (and optional identification) at 104 of the encountered pathogen(s). An example type of purification unit that can be utilized here is a high efficiency particulate air (HEPA) purifier, which is effective at trapping mold and bacteria. Another example type of purification unit is an active carbon system which is effective against chemical emissions, VOCs, and gases by collecting and trapping those particulates. Alternatively, ultraviolet (UV) systems can be utilized to kill bacteria and viruses rather than trapping them. This disclosure contemplates using these systems independently or in combination with one another.

The type and location of the environment may also aid in determining which purification unit to select. For example, hospitals and healthcare facilities are susceptible to pathogens such as Methicillin-resistant *Staphylococcus aureus* (MRSA), *Staphylococcus Aureus* (Staph), and legionnaire's disease. Grocers, restaurants, and food industry professionals are susceptible to biofilms, *Listeria, Salmonella, E. Coli*, and VOCs like ethylene gas which breaks down and prematurely ripens produce. Some research suggests that oxygen, carbon dioxide, and other chemical levels in the environment may have significant effects on ripening of produce. As a result, a peroxide formula can be used to potentially reduce the amount of ethylene gas, thereby reducing the rate of ripening of produce (which would be beneficial for grocery stores, markets, etc.) Further, a peroxide formula described herein can be used to reduce the levels of methane gas in environments, making the present process beneficial in environments such as facilities that house livestock, and other applications that generate methane gas. The reduction in methane is particularly useful in locations that have government regulated methane level requirements.

Example purification units can comprise a continuous infectious microbial reduction device which continuously disinfects viruses, bacteria, mold, and other fungi by producing 0.02 parts per million (ppm) of hydrogen peroxide gas from oxygen and water vapor in the air. By way of example, a purification unit can create hydrogen peroxide gas, e.g., in an amount of 0.02 ppm, from the oxygen and humidity already in the air. The hydrogen peroxide gas is then supplied to an affected area. In this manner, the hydrogen peroxide gas diffuses into the affected area, disinfecting present microbes. In some embodiments, positive air pressure devices can disperse or otherwise affect flow of the hydrogen peroxide gas. Another example purification device comprises a proactive surface and air purification system.

Further referencing FIG. 1, the purification process at 110 further comprises placing at 116 the purification unit (or units) in order to treat a predetermined area of the indoor environment. Determination for the locational placement of the purification unit (or units) will vary based on a variety of factors such as structure of the environment and/or size of the environment. One example embodiment comprises placing the purification unit(s) in an indoor environment's heating, ventilation, and air conditioning (HVAC) distribution system. Placement in the HVAC distribution system allows the purification unit to operate, monitor, and influence a larger area, or an indoor environment which contains multiple separate spaces. An alternate example embodiment utilizes each purification unit as a stand-alone device. Benefits of a stand-alone unit include portability, ease of installation/placement, and ease of maintenance. This disclosure contemplates using these placement options both independently or in combination with one another. Once the purification unit has been placed in the environment, the unit is activated. Excluding loss of power/electricity, or intentional shutoff of the purification unit, the purification unit is in operation indefinitely in certain embodiments. In other embodiments, the purification unit is in operation at select times or for a predetermined duration.

In an example implementation, such purification systems provide 24-hour, 365-day protection and prevention from pathogens such as bacteria, mold, virus, and VOCs. As such, the purification units continue working to attack microbes continuously as they are introduced.

Moreover, certain aspects provide monitoring of indoor environments, allowing a user to view contaminant levels in real-time (or near real-time, e.g., within minutes or hours of sample collection), thus providing ongoing documentation of their environment. In some embodiments, a graphical user interface to a system, e.g., via a web portal, app on a smart device, directly on one or more of the above-described hardware components, etc., provides user interaction and up-to-date monitoring. In other embodiments, reports and other monitor reporting are generated by the system and are delivered to a user. In this regard, sensor and data collection features can be used to collect data for local analysis, or the collected data can be communicated, e.g., via wired or wireless connectivity, to a remote computer, e.g., cloud-based processing system including a server computer.

In an additional embodiment of the disclosure, the purification unit assess its maintenance status by running self-diagnostics on itself and/or an external device collects diagnostic information with regard to the purification unit. The diagnostics may assess items such as health of the filters, battery power, and/or health of the components. According to some embodiments, in the event the diagnostics detect an event or events indicative of the need for maintenance, an alert is generated, e.g., to contact a specific person or entity, to automatically schedule a service call, etc. The contacted entity may include the purification unit manufacturer, the entity using the purification unit, the placer/installer of the purification unit, or a combination thereof.

The purification process at 110 further comprises monitoring at 118 the environment by measuring and analyzing for pathogens in the indoor environment. Monitoring can persist, e.g., for weeks, months, years, indefinitely, etc. While the purification unit is operating, the indoor environment is monitored for pathogens, e.g., by measuring and analyzing the environment for pathogens utilizing the same principles described with reference to measuring at 102 and analyzing at 104 disclosed above, or by using different techniques.

This may comprise measuring and analyzing for the same type of pathogen previously detected, by analyzing for a different type of pathogen than that previously detected, by analyzing for a predetermined set of pathogen types, or by analyzing broadly for any pathogens.

In an example embodiment, the indoor environment is continuously (e.g., in a continuous manner, in an otherwise ongoing fashion, periodically, or otherwise as necessary) monitored in real time. As used herein, "continuous" can comprise systematically monitoring the environment. For the purpose of this disclosure, systematic monitoring can include variable monitoring. Systematically, monitoring may be continuous, at set intervals, triggered based upon events, or manually activated. In one embodiment, a monitoring unit systematically monitors the indoor environment for the specific pathogen identified during the initial portions, e.g., measuring at 102 and analyzing at 104, of the process. In a different embodiment, the purification unit systematically monitors the environment for additional pathogens in conjunction with specific pathogens identified during the initial portions of the process, e.g., measuring at 102 and analyzing at 104.

The purification process at 110 further decides at 120 whether a predetermined threshold is exceeded. This may be the same threshold used to determine if the indoor environment is contaminated, or some other threshold, e.g., the lapse of a predetermined amount of time, a detected pathogen, etc.

The process 100 also comprises triggering at 122 an action in response to detecting that the predetermined threshold has been exceeded. In one embodiment, the triggering action is the purification unit releasing a chemical or formula to mitigate the situation, e.g., to mitigate the detected pathogen, to reduce ethylene, to reduce methane, a combination thereof, etc. In an example implementation, the process, upon detecting that black mold has exceeded the predetermined threshold, releases aerosolized peroxide by the purification unit to mitigate the black mold. In another embodiment, the triggering action is the purification unit alerting a specified entity that the pathogen level exceeds the predetermined threshold. The specified entity may include the purification unit manufacturer, the entity using the purification unit, the placer/installer of the purification unit, or a combination thereof.

In this regard, aspects may sanitize at 112, a first area, e.g., an area of detected contamination, and purify at 112 and continue to monitor at 118, that first area. In alternative embodiments, aspects may sanitize a first area at 112, but purify at 116 and monitor at 118, a second area, which can encompass the first area and include additional area(s) within the indoor environment. Thus, the process can clean an area where actual pathogens are measured, but treat and monitor a larger area, including the entirety of an indoor environment.

Moreover, the sanitizing at 112 may address a first pathogen type or group of pathogen types, and the purification at 116 and monitoring at 118 can be carried out on the same pathogen of pathogen types. Alternatively, the sanitizing at 112 may address a first pathogen type or group of pathogen types, and the purification at 116 and monitoring at 118 can address a second pathogen type or second group of pathogen types. In this regard, the second group of pathogen types can include the first pathogen (or first group of pathogen types) and also includes other pathogen types. For instance, a surface may be sanitized to address a specific species of mold. However, the purification and monitoring can be carried out to address the specific species of mold and other species of mold, or to treat mold and other related pathogens generally, etc. Yet further, any combination of the above-described sanitizing at 112, selecting at 114, placing at 116, monitoring at 118, detecting at 120, and triggering at 122 can be carried out.

Figure 2:
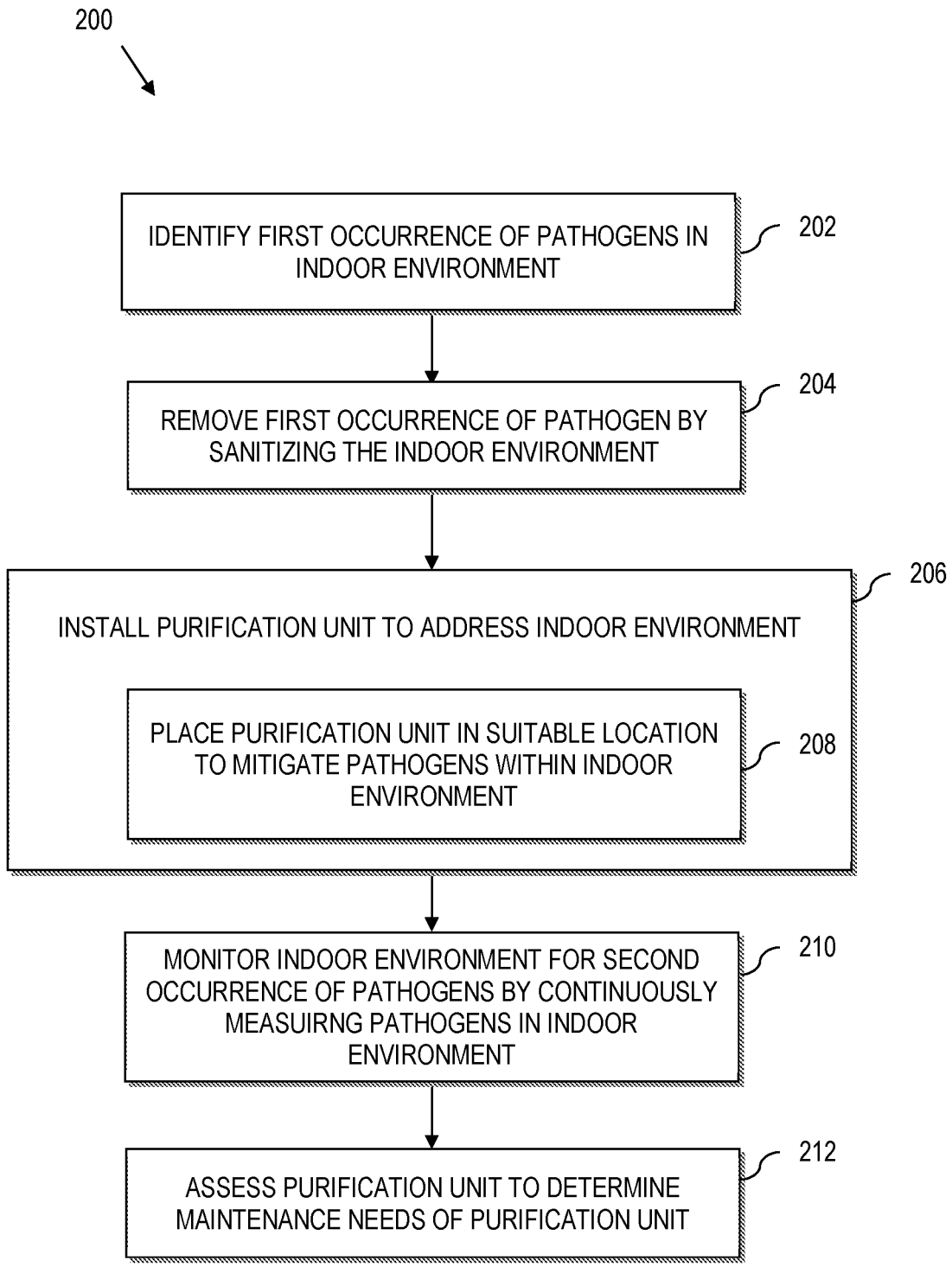
FIG. 2 is a flow chart that illustrates another process for pathogen mitigation according to further aspects of the present disclosure.

Referring to FIG. 2, another process 200 for mitigating indoor pathogens is illustrated. In general, the process 200 can utilize any of the techniques, systems, structures, etc., as set out with regard to the process 100 of FIG. 1, in any combination, except as otherwise expressly noted.

More precisely, the process 200 comprises identifying at 202, a first occurrence of pathogens in an indoor environment, e.g., by measuring the pathogens in the indoor environment. In some embodiments, the identification at 202 utilizes the same techniques and methodologies used in measuring at 102 and/or analyzing at 104 described herein with reference to the process 100.

The process 200 further comprises removing at 204, the first occurrence of pathogen by sanitizing the indoor environment where first occurrence of pathogen is located. In some embodiments, removal at 204 of the pathogen by sanitization utilizes the same techniques and methodologies used in the sanitizing at 112 portion of the purification process at 110 as disclosed in process 100.

The process 200 additionally comprises installing at 206 a purification unit in the indoor environment. In some embodiments, the installation at 206 of the purification unit utilizes the same techniques and methodologies used in selecting at 114 and placing at 116 described herein with reference to the process 100.

For instance, the process 200, and more particularly, installing at 206 can further comprise placing at 208 a purification unit in a suitable location to mitigate pathogens within the indoor environment. In certain embodiments, the placement at 208 of the purification unit utilizes the same techniques and methodologies used in selecting at 114 and/or placing at 116 described herein with reference to the process 100.

The process 200 additionally comprises monitoring at 210, the indoor environment for a second occurrence of pathogens, e.g., by continuously (or otherwise ongoing as defined more fully herein) measuring the pathogens in the indoor environment. Monitoring can persist, e.g., for weeks, months, years, indefinitely, etc. In example embodiments, monitoring at 210 of the indoor environment utilizes the same techniques and methodologies used in monitoring at 118 as described herein with reference to the process 100.

Also, the process 200 comprises assessing at 212, the purification unit to determine the maintenance needs of the purification unit. In an example embodiment of the disclosure, the purification unit self-assesses a maintenance status by running self-diagnostics. In other embodiments, an external source monitors the health of the purification unit(s). The diagnostics may assess items such as health of the filters, battery power, and/or health of the components. In another embodiment, in the event the diagnostics detect one or more events indicative of the need for maintenance, an alert can be generated, examples of which are described more fully with reference to the process 100 of FIG. 1.

Figure 3:
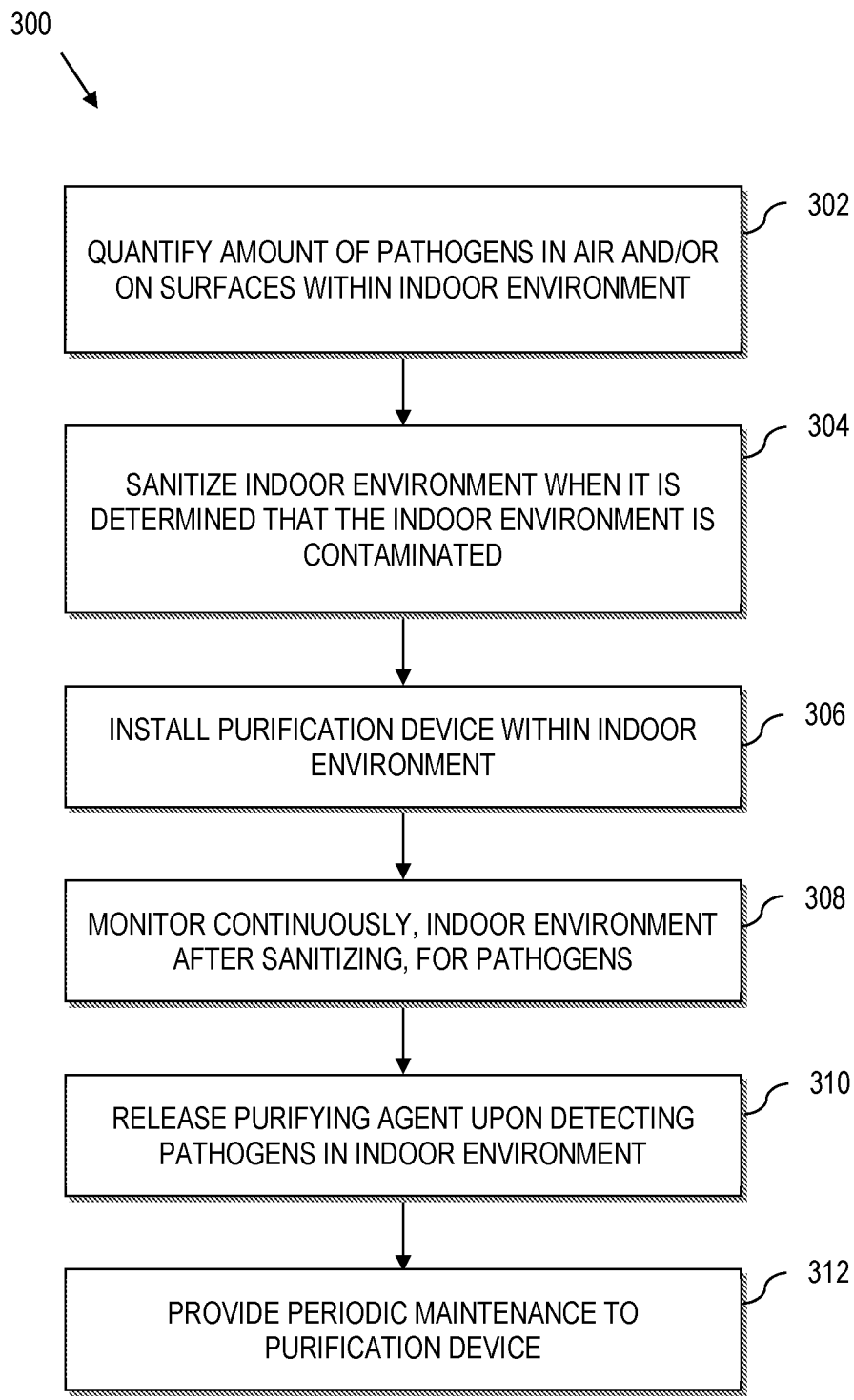
FIG. 3 is a flow chart that illustrates yet another process for pathogen mitigation according to further aspects of the present disclosure.

Referring to FIG. 3, a process 300 for mitigating (which can include remediating) indoor pathogens is illustrated. In general, the process 300 can utilize any of the techniques, systems, structures, etc., as set out with regard to the process 100 of FIG. 1, in any combination, except as otherwise expressly noted.

The process 300, comprises quantifying at 302, e.g., using a bio-aerosol monitoring system, the amount of total pathogens in the air and/or on surfaces within an indoor environment. In some embodiments, quantifying at 302 utilizes the same techniques and methodologies used in measuring at 102 and/or analyzing at 104 as described herein with reference to the process 100.

In an example embodiment, quantifying at 302 is performed by using a bio-aerosol monitoring system that measures the total pathogens in the air and/or on surfaces which evaluates the needs of a space while providing real-time insight through the ongoing measurements.

The process 300 further comprises sanitizing at 304, the indoor environment with portable equipment to stabilize the indoor environment when it is determined that the indoor environment is contaminated. In example embodiments, sanitization at 304 utilizes the same techniques and methodologies used in analyzing at 104 and sanitizing at 112 as described herein with reference to the process 100.

The process 300 additionally comprises installing at 306, a purification device within the indoor environment. In some embodiments, installing at 306 of the purification unit utilizes the same techniques and methodologies used in selecting at 114 and/or placing at 116 as described herein with reference to the process 100.

In an example embodiment, installation at 306 is accomplished by placing a purification device in the vicinity of a contaminated area (or by placing purification devices throughout or in the vicinity of contaminated areas) of the indoor environment either as a stand-alone unit, or via a building's HVAC distribution systems to provide ongoing, e.g., 24-hour, 365 day protection and prevention from pathogens.

The process 300 further comprises monitoring at 308 continuously (or otherwise in an ongoing manner as described more fully herein), the indoor environment, after sanitizing for pathogens. Monitoring can persist, e.g., for weeks, months, years, indefinitely, etc. For the purposes of this disclosure, monitoring at 308 utilizes the same techniques and methodologies used in monitoring at 118 as described herein with reference to the process 100.

In an embodiment, monitoring at 308 further comprises providing a view of contaminant levels in real time. In an alternate embodiment of monitoring at 308, ongoing documentation regarding the indoor environment is given in real time. The views and/or reports are analogous to the views and/or reports described with reference to FIG. 2.

The process 300 additionally comprises releasing at 310, a purifying agent upon detecting pathogens in the indoor environment. In certain embodiments, releasing at 310 utilizes the same techniques and methodologies used in triggering at 122 as described herein with reference to the process 100. In this regard, releasing a purifying agent can also/alternatively be used to reduce levels of gas within an environment, e.g., ethylene, methylene, etc.

The process 300 yet further comprises providing at 312, periodic maintenance to the purification unit. In some embodiments, providing at 312 utilizes the same techniques and methodologies used in assessing at 212 as described herein with reference to the process 200. In an example embodiment, providing at 312 comprises replacing at least one power cell and one filter in the purification device.

Accordingly, various embodiments of the present disclosure provide a total purification solution for indoor environments by incorporating various technologies, processes, and actions in an integrated and deliberate pathogen-specific solution that is uniquely tailored to the contamination infecting a specific indoor environment.

Systems and processes herein are configured to measure, remove, and reduce dangerous pathogens like bacteria, mold, viruses, and volatile organic compounds (VOCs). Systems and processes herein can also prevent dangerous pathogens like bacteria, mold, viruses, and volatile organic compounds (VOCs) from recurring through ongoing service. Certain embodiments can be deployed while people are still occupying the indoor environment, thus allowing people to go about their daily routines without disruption or risk of health hazards.

Systems and processes herein enable hospitals and healthcare facilities to diffuse contaminants before outbreaks occur, reduce the spread MRSA, staph, legionnaires and other harmful pathogens, improve the health of employees and patients, reduce inventory waste, and reduce missed work days. Grocers and restaurants can utilize the systems and processes herein to reduce or eliminate harmful biofilms, *Listeria, Salmonella, E. Coli*, etc., which may otherwise be present on fruits and vegetables, thus reducing waste. Yet further, systems and processes herein can reduce VOCs such as ethylene gas that breaks down and ripens produce (ex. fruit) prematurely. As such, food industry professionals can protect food during production, transport, and storage, and extend product shelf life. Moreover, homeowners and families can remain healthy and safe.

Figure 4:
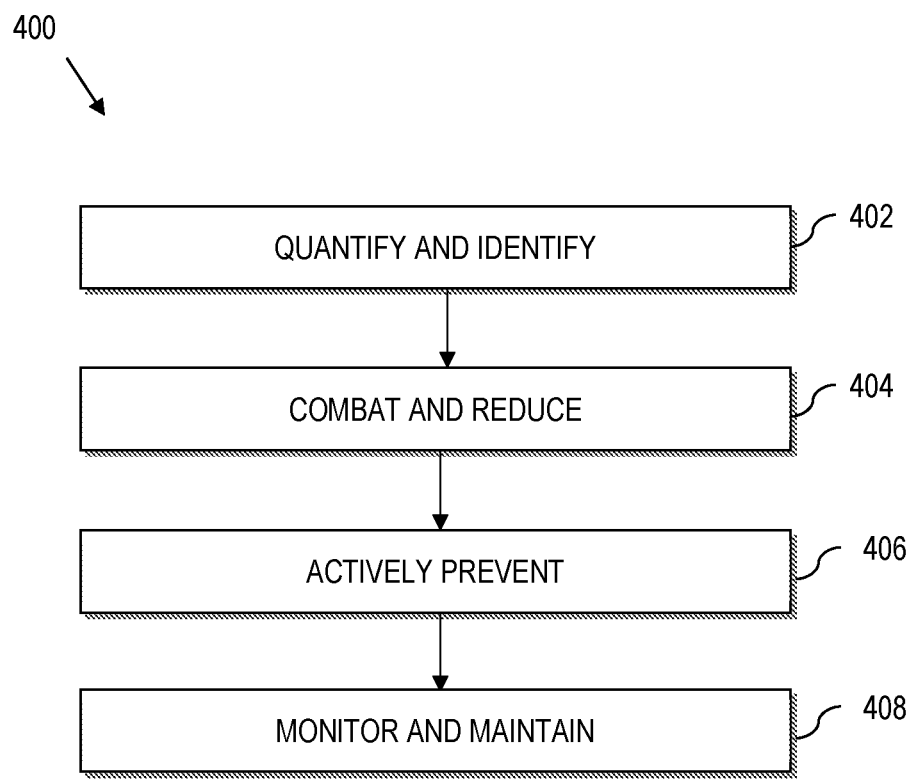
FIG. 4 is a flow chart of an example process for addressing pathogen mitigation according to yet further aspects of the present disclosure.

Referring now to FIG. 4, a process 400 illustrates yet another process for mitigating pathogens. In general, the process 400 can utilize any of the techniques, systems, structures, etc., as set out with regard to the process 100 of FIG. 1, in any combination, except as otherwise expressly noted.

The process 400 comprises quantification and identification at 402. In an example embodiment, a device such as a bacteria and biofilm scanner, such as a fluorescent lamp, can be used to identify a location of contaminants, such as biofilms, mold, bacteria, other contaminants, etc. In this regard, contaminants can be detected even on solid surfaces, using no consumables. In addition, or alternatively, a bioaerosol monitoring device can be used as described more fully herein, e.g., with reference to FIG. 1-FIG. 3. Using a bioaerosol monitoring system, the process at 402 can measure total pathogens found in the air that are both viable and non-viable. Additional information that can be gathered includes size, quantity, etc., of living airborne particulates.

The process 400 also comprises combating and reducing at 404, contaminants. For instance, the environment can be cleaned, examples of which are set out more fully herein with reference to FIG. 1-FIG. 3. In this regard, the process 400 can use cleaning units that provide validated results without production down time. The combat and reduction at 404 can be used to stabilize an area and reduce the risk of having contamination affect people, goods, products, etc.

The process 400 actively prevents at 406, the contamination from spreading, growing, returning, or otherwise adversely affecting the area. For instance, the process 400 installs at least one purification device, e.g., as set out more fully herein with reference to FIG. 1-FIG. 3. In example embodiments, purification devices can be installed throughout an affected area (or areas) either as stand-alone hardware or deployed via a building HVAC distribution system. This approach can be utilized to provide 24 hours a day, 7 days a week, preventative measures, which can prevent or otherwise reduce the risk associated with pathogens such as *Listeria, E. Coli, Salmonella*, mold, etc.

The process 400 monitors and maintains at 408. Monitoring can persist, e.g., for weeks, months, years, indefinitely, etc. By collecting ongoing e.g., continuous, periodic, triggered, etc., measurements and ongoing documentation of the environmental status in view of the process 400, an entity can monitor an indoor environment, e.g., in real-time or otherwise.

The process 400 may provide preventive measures but may or may not be able to provide complete disinfection and/or sterilization of all particulates, depending upon the requirements and equipment used to implement the process 400.

Figure 5:
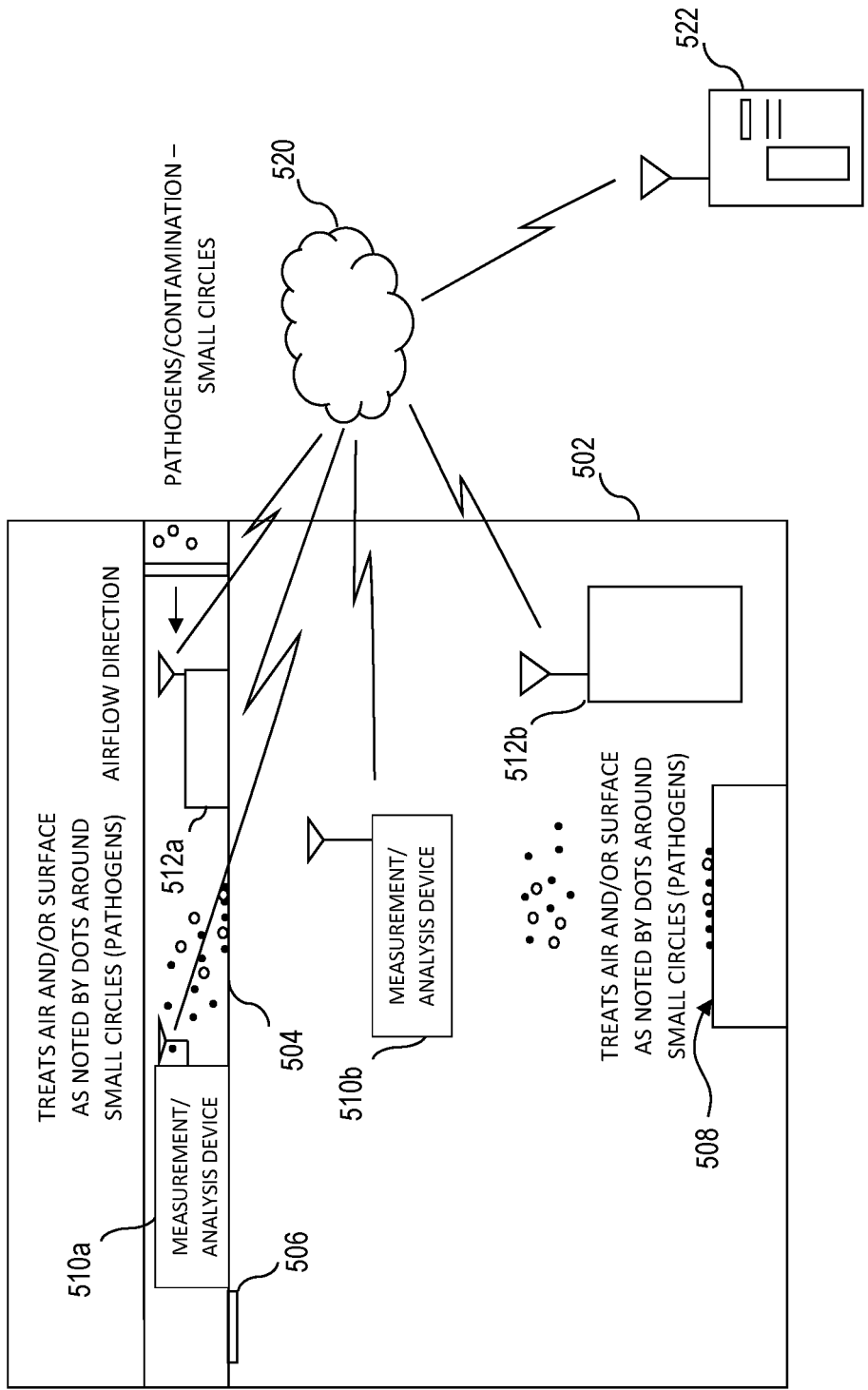
FIG. 5 is a block diagram of an example indoor environment to illustrate aspects of the processes set out more fully herein.

Referring to FIG. 5, an example indoor environment 502 is illustrated in schematic form. The indoor environment 502 comprises an HVAC distribution system, e.g., schematically illustrated by ductwork 504 and vent 506. The indoor environment 502 also includes surfaces, e.g., schematically illustrated by the surface 508.

Initially, measurement and analysis processes are carried out, e.g., using a measurement and analysis device (or devices) 510 as described more fully with reference to FIG. 1-FIG. 4. For sake of clarity, a measurement and analysis device 510a is illustrated in the ductwork 504 of an HVAC distribution system. Alternatively (or additionally), a measurement and analysis device 510b is positioned in a volume within the indoor environment 502 depending upon the application. While schematically shown for convenience as a single device that measures and analyzes, in practice, measurement and analysis can be two or more devices, which can include computers, processors, controllers, intakes, etc., as described more fully with reference to FIG. 1-FIG. 4 above.

If the measurement and analysis device 510 identifies a contamination (schematically represented by small circles), a sanitization process is carried out, along with the selection, placement and continued operation of one or more purification units, described more fully with reference to FIG. 1-FIG. 4. For instance, as schematically illustrated, contaminants are in the ductwork 504. As such, a purification unit, e.g., purifying device 512a, filter 514, combination thereof, etc., are deployed in the ductwork 504. The purifying device 512a can treat the air, surfaces, or a combination thereof, as schematically illustrated by the solid dots surrounding the small circles (pathogens).

For sake of illustration, a second purifying device 512b is illustrated within a volume of the indoor environment 502. Analogous to that above, the second purifying device 512b can treat the air and/or surfaces 508 as illustrated by the dots surrounding the small circles (pathogens). The purifying device 512 (e.g., first purifying device 512a and second purifying device 512b) can be implemented using any combination of sanitizing and/or purifying devices described more fully herein with reference to FIG. 1-FIG. 4.

During monitoring, the measurement and analysis devices 510 can be the same devices used for initial measurement and analysis, or the measurement and analysis devices can be different for the ongoing monitoring. In some embodiments, e.g., at set intervals, a measurement device 510 can be returned to take new measurements, to carry out relatively more robust monitoring and analysis, etc., than that used for continued maintenance of the indoor environment. Further, during monitoring, the measurement and analysis devices 510 may measure and analyze for pathogens other than the pathogen initially identified.

As noted above, reports, maintenance requests, data collection, etc., can be carried out either locally or remotely. By way of example, one or more of the measurement and analysis device 510a, measurement and analysis device 510b, purifying device 512a, purifying device 512b, etc., can communicate (e.g., wired or wirelessly) across a network 520 (local intranet, Internet, combination thereof, etc.). As such, a remote server 522 can monitor the process, determine when alerts are triggered, determine when maintenance is required, dispatch service, additional sanitizing efforts, etc., as described more fully herein. In some embodiments, the various components communicate with themselves, e.g., communicate locally or through the network 520, thus allowing tight cohesion between purification, monitoring, and triggering actions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Aspects of the disclosure were chosen and described in order to best explain the principles of the disclosure and the practical application, and to enable others of ordinary skill in the art to understand the disclosure for various embodiments with various modifications as are suited to the particular use contemplated.

What is claimed is:

1. A process for mitigating indoor pathogens, the process comprising:
    measuring, using a pathogen measurement device, for pathogens in an indoor environment;
    analyzing the measurements to identify whether the indoor environment is contaminated with a pathogen; and
    performing a purification process in response to determining that the indoor environment is contaminated, the purification process comprising:
        sanitizing at least a portion of the indoor environment to mitigate contamination of detected pathogens;
        selecting a purification unit for the indoor environment based upon the identified contamination caused by detected pathogens, wherein the purification unit is placed in order to treat a predetermined area of the indoor environment, the purification unit engaged to operate after sanitizing;
        monitoring the indoor environment by measuring for pathogens in the indoor environment; and
        triggering an action in response to detecting a pathogen level that exceeds a predetermined threshold.

2. The process of claim 1, wherein measuring pathogens comprises measuring an amount of pathogens in the air.

3. The process of claim 1, wherein measuring pathogens comprises measuring an amount of pathogens on a surface.

4. The process of claim 3, wherein measuring for pathogens in an indoor environment comprises using a bio-aerosol monitoring process.

5. The process of claim 1, wherein sanitizing at least a portion of the indoor environment comprises releasing charged ions and hydrogen peroxide gas targeted to the location of detected pathogens.

6. The process of claim 1 further comprising placing the selected purification unit in the indoor environment's heating, ventilation, and air conditioning (HVAC) distribution system.

7. The process of claim 1, wherein further comprising placing the selected purification unit in the indoor environment in the form of a stand-alone device.

8. The process of claim 1, wherein:
monitoring the indoor environment by measuring for pathogens in the indoor environment comprises systematically monitoring the indoor environment for pathogens.

9. The process of claim 8, wherein systematically monitoring the indoor environment for pathogens comprises systematically monitoring the indoor environment for pathogens other than the detected pathogen that had previously contaminated the indoor environment.

10. The process of claim 9, wherein selecting a purification unit comprises selecting a purification unit based on the detected pathogen and the pathogens other than the detected pathogen.

11. The process of claim 1 further comprising:
communicating, wirelessly over a network, between the pathogen measurement device and a remote server; and
communicating, wirelessly over the network, between the selected purification device and the remote server.

12. The process of claim 1 further comprising:
communicating, wirelessly over a network, between the pathogen measurement device and the selected purification device.

13. The process of claim 1, wherein triggering an action in response to detecting a pathogen level that exceeds a predetermined threshold comprises releasing a chemical to mitigate the detected pathogens.

14. The process of claim 1, further comprising:
assessing the purification unit to determine maintenance needs by running component diagnostics on the purification unit; and
alerting a specified party when a component needs to be replaced.

15. A process for mitigating indoor pathogens, the process comprising:
quantifying, using a bio-aerosol monitoring system, an amount of total pathogens in the air and/or on surfaces within an indoor environment;
sanitizing the indoor environment with portable equipment to stabilize the indoor environment when it is determined that the indoor environment is contaminated;
installing a purification device to address a contaminated area of the indoor environment;
monitoring continuously, the indoor environment after sanitizing, for pathogens;
releasing a purifying agent upon detecting pathogens in the indoor environment; and
providing periodic maintenance to the purification device.

16. The process of claim 15, wherein:
quantifying, using a bio-aerosol monitoring system, the amount of total pathogens in the air and on surfaces further comprises evaluating the needs of a treated space; and
providing real-time insight through ongoing measurements.

17. The process of claim 15, wherein:
installing purification devices throughout contaminated areas of the indoor environment comprises installing either a standalone hardware system or system deployed via a building's heating, ventilation, and air conditioning distribution systems to provide 24-hour, 365-day protection and prevention from pathogens comprising at least one of bacteria, mold, virus, and volatile organic compounds.

18. The process of claim 15, wherein:
monitoring continuously, the indoor environment after sanitizing, for pathogens comprises providing a view of contaminant levels in real time.

19. The process of claim 15, wherein:
monitoring continuously, the indoor environment after sanitizing, for pathogens comprises providing ongoing documentation of the indoor environment.

* * * * *